United States Patent
Guan et al.

(10) Patent No.: US 6,596,897 B1
(45) Date of Patent: Jul. 22, 2003

(54) CATALYST FOR PRODUCING ACRYLONITRILE

(75) Inventors: Xingya Guan, Shanghai (CN); Xin Chen, Shanghai (CN); Lianghua Wu, Shanghai (CN)

(73) Assignees: China Petro-Chemical Corporation, Beijing (CN); Research Institute of Petroleum Processing, Beijing (CN)

( * ) Notice: Subject to any disclaimer, the term of this patent is extended or adjusted under 35 U.S.C. 154(b) by 0 days.

(21) Appl. No.: 09/508,038

(22) PCT Filed: Aug. 12, 1998

(86) PCT No.: PCT/CN98/00165
§ 371 (c)(1),
(2), (4) Date: Jun. 30, 2000

(87) PCT Pub. No.: WO99/11368
PCT Pub. Date: Mar. 11, 1999

(30) Foreign Application Priority Data

Sep. 3, 1997 (CN) .......................................... 97106580 A

(51) Int. Cl.$^7$ ...................... C07C 253/00; B01J 27/192; B01J 21/08; B01J 21/12; B01J 21/14
(52) U.S. Cl. ........................ 558/323; 558/324; 558/325; 558/326; 502/212; 502/248; 502/254; 502/255; 502/311; 502/312; 502/313; 502/314; 502/315; 502/316; 502/321
(58) Field of Search ................................ 502/212, 254, 502/255, 311, 312, 313, 314, 315, 316, 321, 322, 323, 407, 439, 248; 558/323, 324, 325, 326

(56) References Cited

U.S. PATENT DOCUMENTS

| | | | | |
|---|---|---|---|---|
| 3,988,359 A | * | 10/1976 | Saito et al. ............... | 260/465.3 |
| 3,992,419 A | * | 11/1976 | Otaki et al. ............ | 260/346.8 A |
| 4,322,358 A | * | 3/1982 | Bither, Jr. et al. ....... | 260/346.11 |
| 4,423,281 A | * | 12/1983 | Yamamoto et al. ......... | 585/626 |
| 4,438,217 A | * | 3/1984 | Takata et al. ............... | 502/205 |
| 4,442,308 A | * | 4/1984 | Arntz et al. ................. | 568/480 |
| 4,537,874 A | * | 8/1985 | Sato et al. ................... | 502/311 |
| 4,600,541 A | * | 7/1986 | Aoki et al. .................. | 558/321 |
| RE32,484 E | * | 8/1987 | Grasselli et al. ............ | 502/212 |
| 4,732,884 A | * | 3/1988 | Sarumaru et al. ........... | 502/205 |
| 4,873,217 A | * | 10/1989 | Kawajiri et al. ............. | 502/311 |
| 4,916,103 A | * | 4/1990 | Martan et al. ............... | 502/212 |
| 5,093,299 A | * | 3/1992 | Suresh et al. ............... | 502/212 |
| 5,134,105 A | * | 7/1992 | Paparizos et al. ........... | 502/205 |
| 5,177,048 A | * | 1/1993 | Chen et al. .................. | 502/205 |
| 5,212,137 A | * | 5/1993 | Suresh et al. ............... | 502/212 |
| 5,223,469 A | * | 6/1993 | Chen et al. .................. | 502/205 |
| 5,225,389 A | * | 7/1993 | Caillod et al. .............. | 502/205 |
| 5,364,825 A |   | 11/1994 | Neumann et al. ........... | 502/311 |
| 5,491,258 A | * | 2/1996 | Watanabe et al. ........... | 562/538 |
| 5,532,199 A | * | 7/1996 | Watanabe et al. ........... | 502/311 |
| 5,618,974 A | * | 4/1997 | Kurimoto et al. ........... | 562/532 |
| 5,780,664 A | * | 7/1998 | Aoki .......................... | 558/323 |
| 5,892,108 A | * | 4/1999 | Shiotani et al. ............. | 562/532 |

FOREIGN PATENT DOCUMENTS

| | | |
|---|---|---|
| CN | 1021638 c | 7/1993 |
| CN | 1172691 A | 2/1998 |
| EP | 0 018 103 A1 | 10/1980 |
| EP | 0 018 103 B1 | 10/1980 |
| EP | 0 713 724 A1 | 5/1996 |
| EP | 0 714 697 A1 | 6/1996 |
| EP | 0 713 724 B1 | 5/1999 |
| EP | 0 714 697 B1 | 11/2001 |

* cited by examiner

Primary Examiner—Stanley S. Silverman
Assistant Examiner—Cam N. Nguyen
(74) Attorney, Agent, or Firm—Jenkens & Gilchrist, P.C.

(57) ABSTRACT

A fluidized-bed catalyst for producing acrylonitrile by the ammoxidation of propylene, which comprises a silica carrier and a composite having the following formula:

$$A_a C_c D_d Na_f Fe_g Bi_h M_i Mo_{12} O_x$$

wherein A selected from the group consisting of potassium, rubidium, cesium, samarium, thallium and mixtures thereof; C is selected from the group consisting of phosphorus, arsenic, boron, antimony, chromium and mixtures thereof; D is selected from nickel, cobalt or mixtures thereof; M is selected from tungsten, vanadium or mixtures thereof. The catalyst of the present invention particularly suits the use under higher pressure and higher duties, and still maintains very high single-pass yield of acrylonitrile and a high ammonia conversion. This catalyst particularly suits the requirement for existing acrylonitrile plants to raise capacity. For new plants it can also reduce the investment on the catalyst and the pollution.

4 Claims, No Drawings

CATALYST FOR PRODUCING ACRYLONITRILE

The present invention relates to a fluidized-bed catalyst for producing acrylonitrile by the ammoxidation of propylene.

The production of acrylonitrile by the ammoxidation has been developed for more than 30 years and a balance has been approached between the capacity of the acrylonitrile plants and the demand for acrylonitrile. Now the major development tendency of the production of acrylonitrile has been transformed from the construction of new devices to the reformation of existing plants in order to reduce the consumption of the feed stock and raise the capacity. By reformation of existing plants, change to effective catalysts and elimination of the bottleneck in the production process, it is possible to raise the capacity of acrylonitrile by 50–80%, while the investment required is only 20–30% of that of a newly constructed device. The economic benefit is enormous.

Two problems will arise in the reformation of the plant: (1) the reaction pressure in the fluidized reactor will rise; (2) the catalyst loading can not be too heavy. Therefore, the substitution catalyst should have a higher duty for propylene and the capability to endure higher reaction pressures.

The reaction pressure of the fluidized-bed reactor is determined by a resistance of a serious of heat exchangers, towers and piping between the outlet of the reactor and the top of the absorption tower. An increase in the capacity results in an appreciable increase in the amount of the effluent at the outlet of the reactor so that the aforesaid pressure drop is increased. Further, expanding of the heat conduction area in the heat exchangers contributes to additional pressure drop. To meet the requirement of the environmental protection, the waste gas from the top of the absorption tower is not allowed to purge into the atmosphere, and should be passed to a furnace to burn off. Thus, if a suction pump is not used, the pressure at the top of the absorption tower must be raised. Because of the various reasons mentioned above, the operation pressure of the prior reactor will be 0.5–1.0 times higher than the designed value, i.e., reach above 0.08 MPa.

The aforesaid second problem is the duty of the catalyst, i.e. WWH. The definition of WWH is the tons of propylene treated per ton of catalyst per hour. If the duty of the catalyst does not change, the catalyst loading should increase accordingly when the feed to the reactor increases. But the pipe of the cooling water is not high enough in the original design, and therefore the fluidized height in the reactor may exceed the height of the pipe of the cooling water. Moreover, the linear velocity in operation also appreciably increases because the feed to the reactor increases. The combined effect of the two changes may cause the rise of the temperature of the dilute phase in the reactor, the increase in the yield of carbon dioxide and the decrease in the selectivity to acrylonitrile. Therefore, higher WWH of the catalyst can prevent the aforesaid problems from accruing.

Theoretically, the ability of the catalyst to adsorb propylene should be enhanced by raising the WWH of the catalyst, but the theory that a certain element in a catalyst may enhance the ability to absorb propylene is not available. A catalyst with the following composition has been disclosed in the literature CN 1021638C:

$$A_aB_bC_cNi_dCo_eNa_fFe_gBi_hM_iMo_jO_x$$

where A represents potassium, rubidium, cesium, samarium or thallium, B represents manganese, magnesium, strontium, calcium, barium, lanthanum or rare earth; C represents phosphorus, arsenic, boron, antimony or chromium; M represents tungsten or vanadium.

A higher single-pass yield of acrylonitrile can be obtained on the above catalyst, but the duty for propylene is lower and the single-pass yield of acrylonitrile is greatly lowered under higher reaction pressures. Further research shows that components B and M in the above catalyst correlate to the duty and the high-pressure performance of the catalyst. Although some elements of component B act for raising the single-pass yield of acrylonitrile, they have negative effects on the duty and the high-pressure performance of the catalyst and unfavorable to the suitability to operations at higher pressures and higher duties. Moreover, It has been defined in CN 1021638C that the sum of i and j in the above catalyst composite is 12, i.e., a constant. This limitation is canceled in the present invention because according to this limitation, an increase in component M will result in a decrease in component Mo, and this will affect the single-pass yield of acrylonitrile. Moreover, the literature does not report data on the ammonium conversion. Experiments have approved that the ammonia conversion is about 92–93%, which is relatively low.

The objects of the present invention are to provide a novel catalyst for producing acrylonitrile, which is suitable for operations at higher reaction pressures and higher duties, maintains a high single-pass yield of acrylonitrile and has a high ammonia conversion, to overcome the problems of the catalyst of not being able to suit operations at higher reaction pressures and higher duties present in the above literature.

One object of the present invention is to provide a fluidized-bed catalyst for producing acrylonitrile by the ammoxidation of propylene, which comprises a silica carrier and a composite having the following formula:

$$A_aC_cD_dNa_fFe_gBi_hM_iMo_{12}O_x$$

wherein A is at least one selected from the group consisting of potassium, rubidium, cesium, samarium, thallium and a mixture thereof; C is at least one selected from the group consisting of phosphorus, arsenic, boron, antimony, chromium and a mixture thereof; D is selected from nickel and cobalt or a mixture thereof; M is selected from tungsten, vanadium or a mixture thereof;

a is 0.01–1.0, c is 0.01–2.0, d is 0.01–12, f is 0.2–0.7, g is 0.01–8, h is 0.01–6, i is 0.01–9, x is the total number of the oxygen atom for meeting the requirement of the valence of the elements.

The carrier of the catalyst is silica, the content of which is 30–70% by weight.

Another object of the present invention is to provide a process for producing acrylonitrile by the ammoxidation of propylene at higher reaction pressure and higher duties, wherein the catalysts as above-said are used in a fluidized bed fulfilling the ammoxidation of propylene.

In the above technical solution, the preferred range of a is 0.03–0.4, the preferred range of c is 0.1–1.5, the preferred range of d is 0–8, the preferred range of f is 0.3–0.5, the preferred range of g is 0.1–4, the preferred range of h is 0.1–4, the preferred range of i is 0.1–6; the preferred range of the content of the silica carrier is 40–60% by weight.

There is no special requirement for the preparation procedure of the catalyst of the present invention and the catalyst can be prepared by the conventional procedure. First, various components are made into a solution, which is then made into a slurry by mixing with the carrier. The slurry is shaped into fine spheres via spray drying. Lastly, the fine spheres are calcined to obtain the catalyst. The preparation of the slurry is preferably made according to the procedure in CN 1005248C.

The chemicals for preparing the catalyst of the present invention are:

Component A is preferably the nitrate, hydroxide or salts that can decompose to oxides.

Phosphorus, arsenic, and boron of component C are preferably used in the form of their corresponding acids or ammonium salts. Chromium is preferably used in the form of chromium (III) oxide, chromium nitrate, or a mixture thereof. Antimony may be used in the form of antimony (III) oxide, antimony (V) oxide; antimony halides or antimony sol that are able to hydrolyze to antimony oxides.

Components nickel, cobalt, iron, bismuth can be used in the form of nitrates, oxides, or the salts that are able to decompose to oxides, but water-soluble nitrates are preferable.

Tungsten in component M can be used in the form of ammonium tungstate or tungsten oxide, and vanadium in the form of ammonium metavanadate.

The molybdenum component in the catalyst can be used in the form of molybdenum oxide or ammonium molybdate.

Silica sol, silica gel or the mixture thereof can be used as the starting material of silica that serves as a carrier. If silica sol is used, its quality must accord with the requirement of CN 1005248C.

The prepared slurry is sprayed drying after concentrated by heating to a solid content of 47–55%. The spray drier can be pressure type, dual-flow type, or centrifugal rotary disc type, but the centrifugal type is preferable, which can ensure that the ready catalyst has a good distribution of the particle size.

Calcination of the catalyst can be carried out in two stages: decomposition of the salts of various elements in the catalyst and high-temperature calcination. The temperature of the decomposition is preferably 200–300° C., and the duration is 0.5–2 h. The calcination temperature is 500–800° C., preferably 550–650° C., and the calcination duration is 20 min to 2 h. The aforesaid decomposition and calcination can be carried out separately in two furnaces, or in two zones of one furnace, or simultaneously in a continuous rotary calcination furnace. During the decomposition and calcination of the catalyst, a certain amount of air should be introduced to prevent the catalyst from excessive reduction.

The standers of propylene, ammonia, and molecular oxygen required for producing acrylonitrile by using the catalyst of the present invention are the same as when other catalysts for the ammoxidation are used. Although the content of lower parafins in propylene has no effect on the reaction, from the economic viewpoint, the concentration of propylene is preferably higher than 85% by mole. A fertilizer-grade ammonia can be used. As for molecular oxygen, pure oxygen, rich oxygen or air can be used from the technical viewpoint, but from the viewpoints of economy and safety, air is preferred.

The mole ratio of ammonia to propylene in the feed entering the fluidized-bed reactor is in the range of 0.8–1.5, preferably 1.0–1.3. The mole ratio of air to propylene is 8–10.5, preferably 9.0–9.8. If the operation requires more air, this ratio can be increased to 11 without great effect on the reaction. However, from the viewpoint of safety, the excessive oxygen in the reaction gas can not exceed 7% by volume, preferably does not exceed 4%.

When the catalyst of the present invention is used in a fluidized-bed reactor, the reaction temperature is 420–470° C., preferably 435–450° C. The catalyst of the present invention is a catalyst suitable for operation under higher pressures and higher duties, and thus the reaction pressure in the production device can be higher than 0.08 MPa, such as 0.08–0.15 MPa. Even if the reaction pressure is lower than 0.08 MPa, there is no unfavorable effect on the reaction and the single-pass yield of acrylonitrile can further be raised.

The duty (WWH) of the catalyst of the present invention for propylene is 0.06–0.15 $h^{-1}$, preferably 0.07–0.10 $h^{-1}$. Too low a duty not only wastes the catalyst, but also increases the output of carbon dioxide and decreases the selectivity of acrylonitrile. Too high a duty has no practical significance because too little catalyst added makes the heat transfer area of the pipe of the cooling water in the catalyst layer smaller than that required for removal of the reaction heat and thus makes the temperature out of control.

The prior recovering and refining process without any reformation can be used for processing the product produced with the catalyst of the present invention. That is, the unreacted ammonia is removed from the effluent gas of the fluidized-bed reactor by passing through a neutralization tower and then all the organic compounds are absorbed with low temperature water. Highly pure acrylonitrile product is obtained through extractive distillation, decyanation and dehydration of the absorbent liquid.

One of the characteristics of the catalyst of the present invention is the high conversion of ammonia. Conventionally, it is not desired for the acrylonitrile catalyst to have too high conversions of ammonia, because the rate of ammonia oxidation or combustion is higher than that of the ammoxidation of propylene. If the ammonia conversion is too high, there is not enough ammonia to react with propylene so that a great amount of oxidation products of propylene such as acrolein and acrylic acid and the like is formed, which will bring about difficulties in the recovering and refining of acrylonitrile. Therefore, the catalyst with a high ammonia conversion requires a high ammonia to propylene ratio. This is uneconomic. Even at high ammonia conversions, no great amount of oxides is produced at a normal ammonia ratio because the catalyst of the present invention produces less oxidation products from propylene.

Because tungsten in component M favors the increase of the duty of the catalyst and vanadium can improve the performance of the catalyst under higher pressure, removal of some components that have negative effect on the performance under higher pressures and higher duties and increase of the content of tungsten and vanadium provide the catalyst with good performance under a higher pressure (0.15 MPa) and a higher duty (WWH=0.15 $h^{-1}$), and still maintain the single-pass yield of acrylonitrile at a level above 78%, and thereby good results are obtained.

The further description of the present invention will be given bellow with examples.

EXAMPLE 1

8.5 g of the solution of potassium nitrate with a concentration of 20%, 4.3 g of sodium nitrate, 8.2 g of the solution of cesium nitrate with a concentration of 20% and 4.5 g of thallium nitrate are mixed and dissolved to make material (A).

43.7 g of ammonium tungstate is dissolved in 100 ml of 5% ammonia liquor and the resulted solution is mixed with 354.4 g of the solution of ammonium molybdate in 300 ml of hot water to obtain material (B).

135.1 g of iron nitrate is dissolved in 70 ml of water, thereto is added 97.3 g of cobalt nitrate, 257.7 g of nickel nitrate and 81.1 g of bismuth nitrate. This mixture is heated to dissolve the nitrates to give material (C).

Material (A) is mixed with 1250 g of sodium-free silica sol having a concentration of 40% and stabilized by ammonia. While stirring, 12.3 g of phosphoric acid with a concentration of 20% and 8.4 g of chromium (VI) oxide is added to the mixture. After dissolution, materials (B) and (C) are added while stirring.

The resulted slurry is stirred and heated to concentrate to a solid content of about 50% and then sprayed drying with a centrifugal spray drier. The formed fine powders of a sphere shape are calcined in a rotary calcination furnace of 89 mm ID and 1700 mm length at 670° C. for 1 h to yield a catalyst having the chemical composition of $$Mo_{12}W_{1.0}Bi_{1.0}Fe_{2.0}Co_{2.0}Ni_{5.3}Cr_{0.5}P_{0.15}Na_{0.3}K_{0.1}Cs_{0.05}Tl_{0.1}+50\%SiO_2$$

EXAMPLE 2

The catalyst having the following composition is prepared according to the procedure in Example 1:

$$Mo_{12}W_{1.5}Bi_{1.0}Fe_{2.0}Co_{1.0}Ni_{6.3}Cr_{0.5}P_{0.15}Na_{0.3}K_{0.1}Cs_{0.05}Tl_{0.1}+50\%SiO_2$$

where the amount of ammonium tungstate is 65.5 g, that of cobalt nitrate is 48.6 g, that of nickel nitrate is 306.4 g, with the others being the same as in Example 1.

EXAMPLE 3

The catalyst having the following composition is prepared according to the procedure in Example 1:

$$Mo_{12}W_{1.0}V_{0.2}Bi_{1.0}Fe_{2.0}Co_{2.0}Ni_{5.3}Cr_{0.5}P_{0.15}Na_{0.3}K_{0.1}Cs_{0.05}Tl_{0.1}+50\%SiO_2$$

where the amount of ammonium metavanadate is 1.71 g, with the amount of the others being the same as in Example 1.

EXAMPLE 4

The catalyst having the following composition is prepared according to the procedure in Example 1:

$$Mo_{12}W_{1.5}Bi_{1.5}Fe_{2.0}Co_{0.5}Ni_{6.5}Cr_{0.5}P_{0.15}Na_{0.3}K_{0.1}Cs_{0.1}Tl_{0.15}+50\%SiO_2$$

where the amount of ammonium tungstate is 65.5 g, that of bismuth nitrate is 121.7 g, that of cobalt nitrate is 24.3 g, that of nickel nitrate is 316.1 g, that of cesium nitrate is 16.3 g of an aqueous solution with a concentration of 20%, that of thallium nitrate is 6.7 g, with the amount of the others being the same as in Example 1.

EXAMPLE 5

The catalyst having the following composition is prepared according to the procedure in Example 1:

$$Mo_{12}W_{2.0}Bi_{1.7}Fe_{2.0}Co_{0.5}Ni_{6.3}Cr_{0.5}P_{0.1}Na_{0.3}K_{0.1}Sm_{0.1}Tl_{0.2}+50\%SiO_2$$

where the amount of ammonium tungstate is 87.6 g, that of bismuth nitrate is 137.9 g, that of cobalt nitrate is 24.3 g, that of nickel nitrate is 306.4 g, that of phosphoric acid is 8.2 g of an aqueous solution of phosphoric acid with a concentration of 20%, that of samarium nitrate is 17.8 g of an aqueous solution with a concentration of 20%, that of thallium nitrate is 9.0 g, with the amount of the others being the same as in Example 1.

EXAMPLE 6

The catalyst having the following composition is prepared according to the procedure in Example 1:

$$Mo_{12}W_{1.5}Bi_{1.5}Fe_{2.0}Co_{1.0}Ni_{6.0}Cr_{0.5}P_{0.25}Na_{0.3}K_{0.1}Rb_{0.1}Cs_{0.1}+50\%SiO_2$$

where the amount of ammonium tungstate is 65.5 g, that of bismuth nitrate is 121.7 g, that of cobalt nitrate is 48.7 g, that of nickel nitrate is 291.8 g, that of phosphoric acid is 4.8 g of 85% phosphoric acid, that of cesium nitrate is 16.3 g of an aqueous solution with a concentration of 20%, and the thallium nitrate in Example 1 is replaced by 12.3 g of an aqueous solution of rubidium nitrate with a concentration of 20%, with the amount of the others being the same as in Example 1.

EXAMPLE 7

The catalyst having the following composition is prepared according to the procedure in Example 1:

$$Mo_{12}W_{1.5}Bi_{1.0}Fe_{2.0}Co_{0.5}Ni_{7.5}Cr_{0.5}P_{0.25}Na_{0.3}K_{0.1}Rb_{0.1}Cs_{0.1}+50\%SiO_2$$

where the amount of ammonium tungstate is 65.5 g, that of cobalt nitrate is 24.3 g, that of nickel nitrate is 364.8 g, that of phosphoric acid is 4.8 g of an aqueous solution of phosphoric acid with a concentration of 85%, that of cesium nitrate is 16.3 g of an aqueous solution with a concentration of 20%, and thallium nitrate in Example 1 is replaced by 12.3 g of an aqueous solution of rubidium nitrate with a concentration of 20%, with the amount of the others being the same as in Example 1.

COMPARATIVE EXAMPLE 1

The catalyst having the composition of Example 1 in CN 1021638C is prepared using the procedure in Example 1, with the content of the silica carrier being 50%.

$$Mo_{11.5}W_{0.5}Bi_{0.9}Fe_{1.8}Co_{4.0}Ni_{2.3}Mn_{1.0}Cr_{0.4}P_{0.25}Na_{0.3}Rb_{0.1}Cs_{0.5}$$

COMPARATIVE EXAMPLE 2

The catalyst having the composition of Example 3 in CN 1021638C is prepared using the procedure in Example 1, with the content of the silica carrier being 50%.

$$Mo_{11.8}W_{0.2}Bi_{0.9}Fe_{1.8}Co_{4.0}Ni_{2.3}Mn_{1.0}Cr_{0.4}P_{0.15}B_{0.1}Na_{0.3}K_{0.1}Cs_{0.05}Tl_{0.1}$$

Evaluation tests of the catalyst activity. Evaluation tests of the catalyst activity are carried in a fluidized catalyst of 38 mm ID. The reaction pressure is regulated by a pressure regulator at the outlet of the reactor.

Evaluation result 1: Catalyst activity is tested under a higher reaction pressure and a higher duty for propylene.

The catalyst loading is 400 g. The composition of the feed gas: propylene/ammonia/air=1:1.2:9.8, reaction temperature 440° C., reaction pressure 0.14 Mpa, WWH 0.085 h$^{-1}$. The results are as follows:

|  | Single-pass yield (%) | | | | | | | Conversion(%) | |
| --- | --- | --- | --- | --- | --- | --- | --- | --- | --- |
| Catalyst | Acrylo-nitrile | Aceto-nitrile | Hydrogen cyanide | Acro-lein | Acrylic acid | Carbon monoxide | Carbon dioxide | Propy-lene | Ammo-nia |
| CE*1 | 77.7 | 2.5 | 1.9 | 0.5 | 1.4 | 3.3 | 9.5 | 96.8 | 92.1 |
| CE*2 | 77.1 | 2.6 | 2.3 | 0.6 | 1.6 | 3.6 | 9.3 | 97.1 | 91.8 |
| Example 1 | 79.7 | 2.8 | 1.9 | 0.5 | 1.5 | 3.1 | 8.1 | 97.5 | 96.5 |
| Example 2 | 79.4 | 3.1 | 1.1 | 0.5 | 1.5 | 2.7 | 9.4 | 97.6 | 97.1 |
| Example 3 | 79.5 | 2.6 | 2.1 | 0.5 | 1.5 | 3.3 | 8.1 | 97.5 | 97.0 |
| Example 4 | 79.2 | 2.7 | 2.6 | 0.8 | 1.5 | 3.0 | 7.5 | 97.3 | 96.8 |
| Example 5 | 79.5 | 2.8 | 2.2 | 0.4 | 1.3 | 3.2 | 8.7 | 98.1 | 97.3 |
| Example 6 | 79.5 | 3.4 | 1.0 | 0.5 | 1.5 | 2.5 | 9.0 | 97.6 | 97.1 |
| Example 7 | 79.6 | 2.5 | 1.9 | 0.4 | 1.5 | 3.2 | 8.7 | 97.9 | 96.6 |

*Comparative example

Evaluation result 2: Catalyst activity is tested under a normal reaction pressure and a normal duty for propylene. The catalyst loading is 550 g. The composition of the feed gas: propylene/ammonia/air=1:1.2:9.8, reaction temperature 440° C., reaction pressure 0.082 MPa, WWH 0.045 h$^{-1}$. The results are as follows:

|  | Single-pass yield (%) | | | | | | | Conversion(%) | |
| --- | --- | --- | --- | --- | --- | --- | --- | --- | --- |
| Catalyst | Acrylo-nitrile | Aceto-nitrile | Hydrogen cyanide | Acro-lein | Acrylic acid | Carbon monoxide | Carbon dioxide | Propy-lene | Ammo-nia |
| CE*1 | 79.3 | 2.8 | 1.6 | 0.2 | 1.0 | 3.8 | 9.2 | 98.1 | 93.5 |
| CE*2 | 79.5 | 2.9 | 1.4 | 0.3 | 1.1 | 3.5 | 8.9 | 96.7 | 93.0 |
| Example 1 | 80.6 | 2.9 | 2.2 | 0.5 | 1.6 | 3.3 | 8.0 | 99.0 | 97.0 |
| Example 2 | 80.5 | 3.0 | 1.6 | 0.2 | 1.8 | 3.1 | 9.2 | 99.4 | 97.4 |
| Example 3 | 80.4 | 2.7 | 2.1 | 0.5 | 1.8 | 3.5 | 8.1 | 99.0 | 97.5 |
| Example 4 | 81.1 | 3.3 | 0.9 | 0.2 | 1.6 | 2.6 | 8.6 | 99.1 | 97.1 |
| Example 5 | 81.4 | 3.7 | 1.0 | 0.1 | 1.7 | 2.8 | 8.9 | 99.4 | 97.8 |
| Example 6 | 80.8 | 3.2 | 1.2 | 0.3 | 1.7 | 2.7 | 9.0 | 98.9 | 97.5 |
| Example 7 | 80.7 | 3.2 | 1.4 | 0.5 | 1.7 | 2.7 | 8.9 | 99.2 | 97.2 |

*Comparative example

Evaluation result 3: The activity is tested with the catalyst of Example 1 of the present invention under different reaction pressures. The catalyst loading is 400 g. The composition of the feed gas: propylene/ammonia/air= 1:1.2:9.8, reaction temperature 440° C., WWH 0.085 h$^{-1}$. The results are as follows:

| Reaction pressure (MPa) | Single-pass yield (%) | | | | | | | Conversion(%) | |
| --- | --- | --- | --- | --- | --- | --- | --- | --- | --- |
|  | Acrylo-nitrile | Aceto-nitrile | Hydrogen cyanide | Acro-lein | Acrylic acid | Carbon monoxide | Carbon dioxide | Propy-lene | Ammo-nia |
| 0.08 | 79.6 | 2.1 | 2.3 | 2.0 | 2.1 | 2.5 | 7.1 | 97.8 | 97.5 |
| 0.09 | 79.7 | 2.4 | 1.7 | 1.7 | 2.2 | 2.5 | 7.2 | 97.4 | 97.0 |
| 0.10 | 80.1 | 2.1 | 2.7 | 1.1 | 1.6 | 3.2 | 7.5 | 98.3 | 97.1 |
| 0.11 | 79.7 | 2.3 | 2.7 | 0.9 | 1.7 | 3.2 | 7.6 | 98.0 | 96.9 |
| 0.12 | 79.4 | 2.7 | 2.0 | 0.9 | 1.7 | 2.9 | 7.8 | 97.3 | 96.7 |
| 0.13 | 79.4 | 2.6 | 2.5 | 0.5 | 1.6 | 3.2 | 7.7 | 97.5 | 96.5 |
| 0.14 | 79.7 | 2.8 | 1.9 | 0.5 | 1.5 | 3.1 | 8.1 | 97.5 | 96.5 |
| 0.15 | 78.2 | 3.2 | 2.5 | 0.5 | 1.6 | 3.4 | 7.8 | 97.1 | 96.3 |

The above tests show that, compared with the prior art CN 1021638C, the catalyst of the present invention increases the single-pass yield of acrylonitrile by 1.0–1.5%, and increases the conversion of ammonia by 3–4% under a normal pressure and a normal duty, and increases the single-pass yield of acrylonitrile by 1.5–2.0%, and increases the conversion of ammonia by 4–5% under a higher pressure and a higher duty. Moreover, the single-pass yield of acrylonitrile on the catalyst of the present invention is lowered to a less extent than the prior art catalyst when the reaction pressure is raised.

What is claimed is:

1. A fluidized-bed catalyst for producing acrylonitrile by the ammoxidation of propylene, which consists of a silica carrier and a composite having the following formula:

$$A_a C_c D_d Na_f Fe_g Bi_h M_i Mo_{12} O_x$$

wherein A is selected from the group consisting of potassium, rubidium, cesium, samarium, thallium and mixtures thereof;

C is selected from the group consisting of phosphorus, arsenic, boron, antimony, chromium and mixtures thereof;

D is nickel, cobalt or mixtures thereof;

M is vanadium or a mixture of vanadium and tungsten;

a is 0.01–1.0, c is 0.01–2.0, d is 0.01–12, f is 0.2–0.7, g is 0.01–8, h is 0.01–6, i is 0.01–9, x is the total number of the oxygen atom for meeting the requirement of the valence of the elements; and wherein the content of the carrier in the catalyst is 30–70% by weight.

2. A fluidized-bed catalyst for producing acrylonitrile by the ammoxidation of propylene according to claim 1, wherein a is 0.03–0.4, c is 0.1–1.5, d is 0.1–0.8, f is 0.3–0.5, g is 0.1–4, h is 0.1–4, and i is 0.1–6.

3. A fluidized-bed catalyst for producing acrylonitrile by the ammoxidation of propylene according to claim 1, wherein the content of the silica carrier in the catalyst is 40–60% by weight.

4. A process for producing acrylonitrile by the ammoxidation of propylene at higher reaction pressure and higher duties using the catalysts according to anyone of claims 1–3, wherein the reaction pressures are in the range of 0.08–0.15 MPa and the duties of propylene (WWH) are in the range of 0.06–0.15 $h^{-1}$.

* * * * *